(12) United States Patent
Wilson et al.

(10) Patent No.: US 10,363,336 B2
(45) Date of Patent: Jul. 30, 2019

(54) METHODS AND SYSTEMS FOR TREATING LIQUIDS USING SWITCHABLE SOLVENTS

(75) Inventors: Aaron D. Wilson, Idaho Falls, ID (US); Frederick F. Stewart, Idaho Falls, ID (US); Mark L. Stone, Idaho Falls, ID (US)

(73) Assignee: BATTELLE ENERGY ALLIANCE, LLC, Idaho Falls, ID (US)

( * ) Notice: Subject to any disclaimer, the term of this patent is extended or adjusted under 35 U.S.C. 154(b) by 1613 days.

(21) Appl. No.: 13/480,053

(22) Filed: May 24, 2012

(65) Prior Publication Data

US 2013/0048561 A1 Feb. 28, 2013

Related U.S. Application Data

(60) Provisional application No. 61/527,944, filed on Aug. 26, 2011.

(51) Int. Cl.
*A61L 9/16* (2006.01)
*B01D 61/00* (2006.01)
(Continued)

(52) U.S. Cl.
CPC .............. *A61L 9/16* (2013.01); *B01D 61/002* (2013.01); *B01D 61/005* (2013.01); *C02F 1/445* (2013.01);
(Continued)

(58) Field of Classification Search
CPC .. B01D 61/002; B01D 61/005; B01D 61/025; B01D 61/04; B01D 61/10; B01D 61/58;
(Continued)

(56) References Cited

U.S. PATENT DOCUMENTS

| 5,041,227 A | 8/1991 | van Eikeren et al. |
| 7,560,029 B2 | 7/2009 | Mc Ginnis |

(Continued)

FOREIGN PATENT DOCUMENTS

| CN | 101148984 | 3/2008 |
| WO | 2011/050469 | 5/2011 |

(Continued)

OTHER PUBLICATIONS

PCT International Search Report and Written Opinion of the International Searching Authority for PCT/US2012/051398, dated Nov. 5, 2012, 10 pages.

(Continued)

*Primary Examiner* — Kara M Peo
(74) *Attorney, Agent, or Firm* — TraskBritt (57) ABSTRACT

A method of treating a liquid. The method comprises providing a feed liquid comprising at least one solvent and at least one solute to a first side of a membrane. A single-phase draw solution comprising at least one of an aminium salt, an amidinium salt, and a guanidinium salt is provided to a second side of the membrane. The at least one solvent is osmosed across the membrane and into the single-phase draw solution to form a diluted single-phase draw solution. At least one of $CO_2$, $CS_2$, and COS is removed from the diluted single-phase draw solution to form a first multiple-phase solution comprising a first liquid phase comprising the at least one solvent, and a second liquid phase comprising at least one of an amine compound, an amidine compound, and a guanidine compound. A liquid purification system is also described.

25 Claims, 5 Drawing Sheets

(51) Int. Cl.
*C02F 1/44* (2006.01)
*C02F 103/06* (2006.01)
*C02F 103/08* (2006.01)

(52) U.S. Cl.
CPC .......... *C02F 1/441* (2013.01); *C02F 2103/06* (2013.01); *C02F 2103/08* (2013.01)

(58) Field of Classification Search
CPC ........ B01D 2311/04; B01D 2311/2653; B01D 2311/2661; B01D 2311/2665; C02F 1/44; C02F 1/441; C02F 1/445; C02F 9/00
See application file for complete search history.

(56) References Cited

U.S. PATENT DOCUMENTS

| | | |
|---|---|---|
| 7,982,069 B2 | 7/2011 | Jessop et al. |
| 2006/0144789 A1 | 7/2006 | Cath et al. |
| 2008/0058549 A1 | 3/2008 | Jessop et al. |
| 2010/0155329 A1 | 6/2010 | Iyer |
| 2011/0203994 A1* | 8/2011 | McGinnis et al. ............ 210/650 |
| 2011/0257334 A1 | 10/2011 | Jessop et al. |
| 2012/0267308 A1 | 10/2012 | Carmignani et al. |

FOREIGN PATENT DOCUMENTS

| | | |
|---|---|---|
| WO | 2011/097727 | 8/2011 |
| WO | 2012/079175 | 6/2012 |

OTHER PUBLICATIONS

Cath et al., "Forward osmosis: Principles, applications, and recent developments," Journal of Membrane Science 281 (2006) 70-87.
Jessop et al., "A solvent having switchable hydrophilicity," Green Chem., 2010, 12, 809-814.
Jessop et al., "Green chemistry: Reversible nonpolar-to-polar solvent," Nature, 2005, 436, 1102.
Jessop et al., "Tertiary amine solvents having switchable hydrophilicity," Green Chem., 2011, 13, 619-623.
Jessop, Philip G., "Searching for green solvents," Green Chem., Feb. 7, 2011, DOI: 10.1039/c0gc00797h, 8 pages.
McCutcheon et al., "A novel ammonia-carbon dioxide forward (direct) osmosis desalination process," Desalination 174 (2005) 1-11.
McCutcheon et al., "Desalination by ammonia-carbon dioxide forward osmosis: Influence of draw and feed solution concentrations on process performance," Journal of Membrane Science, 2006, 278, 114-123.
McGinnis et al., "Energy requirements of ammonia-carbon dioxide forward osmosis desalination," Desalination, 2007, 207, 370-382.
Phan et al., "Switchable Solvents Consisting of Amidine/Alcohol or Guanidine/Alcohol Mixtures," Ind. Eng. Chem. Res 2008, 47, 539-545.
Wilson, A.D., Rational Design of Next-Generation Nanomaterials and Nanodevices for Water Applications: Design of the Next-Generation FO Draw Solution. International Water Association. 103-130 (2016).
Wilson, A.D., Stewart, F.F., Deriving Osmotic Pressures of Draw Solutes Used in Osmotically Driven Membrane Processes. Journal of Membrane Science 431, 205-211 (2013).
Wilson, A.D., Stewart, F.F., Structure—Function Study of Tertiary Amines as Switchable Polarity Solvents. RSC Adv. 4, 11039-11049 (2014).
Wilson, A.D., Orme, C.J., Concentration Dependent Speciation and Mass Transport Properties of Switchable Polarity Solvents. RSC Adv. 5, 7740-7751 (2015).
McNally, J.S., Wang, X., Hoffmann, C., Weinhold, F., Klein, R., Wilson, A.D. Solution-State Micro-Structuring Through Anti-Electrostatic Hydrogen Bonds (AEHB) and Organic Domains in Molecular Ions (publication forthcoming).
Zapp, K.-H., Wostbrock, K.-H., Schäfer, M., Sato, K., Seiter, H., Zwick, W., Creutziger, R., Leiter, H. Ammonium Compounds, in Ullmann's Encyclopedia of Industrial Chemistry 3, 263-287 (2000).

\* cited by examiner

METHODS AND SYSTEMS FOR TREATING LIQUIDS USING SWITCHABLE SOLVENTS

CROSS-REFERENCE TO RELATED APPLICATIONS

This application claims the benefit of U.S. Provisional Patent Application Ser. No. 61/527,944, filed Aug. 26, 2011, the disclosure of which is hereby incorporated herein in its entirety by this reference.

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The present disclosure, in various embodiments, relates to methods and systems for treating a liquid to purify or concentrate at least one of a solvent and a solute therein. More specifically, embodiments of the present disclosure relate to methods and systems of treating a liquid using a switchable solvent as a draw solute.

BACKGROUND

Decreasing water supplies throughout much of the industrialized world necessitate new methods and systems for utilizing water including contaminants or impurities. Additionally, certain industries have a need for safer, more energy efficient methods and systems for removing water from a target material or solute. Traditional methods and systems of liquid treatment include thermal flash evaporation and membrane filtration. The most popular membrane filtration method is reverse osmosis, in which water is separated from solutes (e.g., contaminants) in a feed liquid by application of a pressure overcoming the osmotic pressure of the feed liquid. For water desalination processes, the pressure to overcome the osmotic pressure of the feed liquid can be substantial, such as greater than 50 atm, resulting in significant equipment and energy costs. Additionally, the application of pressure often exacerbates reverse osmosis membrane fouling by inorganic and organic molecules.

Forward osmosis circumvents several of the deficiencies of reverse osmosis by using osmotic pressure gradients across a semi-permeable membrane to diffuse water from the feed liquid into a draw solution. The enabling feature of the draw solution is a draw solute that enables the draw solution to have a greater osmotic pressure than the feed liquid. Conventional draw solutes include sulfur dioxide, aluminum sulfate, sugars (e.g., glucose, fructose, sucrose), potassium nitrate, ammonium carbonate, and ammonium carbamate. Disadvantageously, such draw solutes either require energy intensive processes, such as reverse osmosis, in order to be removed from the water they draw, or produce materials (e.g., $SO_2$, gaseous ammonia) that are toxic, volatile, and correspondingly expensive to handle.

It would, therefore, be desirable to have a method and system of liquid treatment utilizing an effective, relatively less toxic, and relatively less volatile draw solute that is easily removed following forward osmosis. Such a method and system would reduce the energy demands and operational costs associated with conventional liquid treatment technologies, favorably affecting a broad array of operations such as bulk water purification (water desalination), produced water (e.g., waters brought to the surface during oil and gas drilling) utilization, solution mining (e.g., mining of underground, water-soluble minerals), carbon dioxide scrubbing, and acid gas scrubbing.

BRIEF SUMMARY

Embodiments described herein include methods of treating a liquid to purify or concentrate at least one of a solvent and a solute therein, and related systems. In accordance with one embodiment described herein, a method of treating a liquid comprises delivering a feed liquid comprising at least one solvent and at least one solute to a first side of a membrane. A single-phase draw solution comprising at least one of an aminium salt, an amidinium salt, and a guanidinium salt is provided to a second side of the membrane. The at least one solvent is osmosed across the membrane and into the single-phase draw solution to form a diluted single-phase draw solution. At least one of $CO_2$, $CS_2$, and COS is removed from the diluted single-phase draw solution to form a first multiple-phase solution comprising a first liquid phase comprising the at least one solvent, and a second liquid phase comprising at least one of an amine compound, an amidine compound, and a guanidine compound.

In additional embodiments, a method of liquid treatment comprises diffusing water from a feed solution through a semi-permeable membrane and into a draw solution comprising a hydrophilic solvent and at least one of water and alcohol, the hydrophilic solvent comprising at least one of an aminium cation, an amidinium cation, and a guanidinium cation, and at least one of a bicarbonate anion, a carbonate anion, and an alkyl carbonate anion to form a diluted draw solution. The diluted draw solution is exposed to at least one of heat, reduced pressure, and a non-reactive gas to form a first multiple-phase solution comprising a water phase and a hydrophobic solvent phase comprising at least one of an amine compound, an amidine compound, and a guanidinium compound. The water phase and the hydrophobic solvent phase are separated.

In yet additional embodiments, a liquid treatment system may comprise a forward osmosis device configured to transfer a solvent from a feed liquid into a draw solution to form a diluted draw solution, a first solvent switching area positioned downstream of the forward osmosis device and configured to process the diluted draw solution to produce a first concentrated draw solution and a liquid product, a filtration device positioned downstream of the first solvent switching area and configured to filter the liquid product to form a second concentrated draw solution and a purified liquid product, and a second solvent switching area positioned downstream of the first solvent switching area and the filtration device and configured to process at least one of the first concentrated draw solution and the second concentrated draw solution to produce the draw solution.

BRIEF DESCRIPTION OF THE SEVERAL VIEWS OF THE DRAWINGS

While the specification concludes with claims particularly pointing out and distinctly claiming that which is regarded as the invention, advantages of the invention can be more readily ascertained from the following detailed description when read in conjunction with the accompanying drawings in which:

DETAILED DESCRIPTION

Methods and systems for treating a liquid to purify or concentrate at least one of a solvent and a solute therein using a switchable hydrophilicity solvent (SHS) are disclosed. As used herein, the term "switchable hydrophilicity solvent" means and includes a material that is configured to switch or convert from a hydrophobic form to a hydrophilic form or from a hydrophilic form to a hydrophobic form when subjected to a change in reaction conditions (e.g., the addition or removal of a gas). The hydrophobic form and hydrophilic form of the SHS each have a different solubility in a solvent, such as water. The hydrophilic form may be miscible in the solvent, while the hydrophobic form may be immiscible in the solvent. The SHS may be used as a draw solute to separate or remove a solvent from a feed liquid by forward osmosis or to increase a concentration of at least one solute in the feed liquid. The draw solution including the SHS may have a greater osmotic pressure than the feed liquid, facilitating an osmotic pressure gradient through a semi-permeable membrane to draw the solvent into the draw solution while leaving at least one solute in the feed liquid. The solute may be a contaminant (e.g., impurity) in the feed liquid or may be a desired product in the feed liquid. After receiving the solvent in the draw solution, a change in reaction conditions may enable a majority of the SHS to be separated from the solvent and recovered. The recovered SHS may be recycled for use in additional processes. Trace amounts of SHS remaining in the solvent may be efficiently separated by conventional processes, such as reverse osmosis. The SHS separated from the solvent may be subjected to another change in reaction conditions and may be used to repeat the process. In one embodiment, the SHS may be used to efficiently separate the solvent (e.g., water) from at least one solute (e.g., an inorganic material, an organic material, or an inorganic/organic hybrid material) in the feed liquid. In another embodiment, the SHS may be used to efficiently separate the solvent (e.g., water) from a mixture of at least one inorganic solute material and at least one organic solute material. The methods and systems of liquid treatment disclosed herein may be more energy efficient, less costly, and safer as compared to conventional liquid treatment systems for the purification or concentration of at least one of a solvent and a solute.

The following description provides specific details, such as equipment types, material compositions, and processing conditions in order to provide a thorough description of embodiments of the present disclosure. However, a person of ordinary skill in the art will understand that the embodiments of the present disclosure may be practiced without employing these specific details. Indeed, the embodiments of the present disclosure may be practiced in conjunction with conventional systems and methods employed in the industry. In addition, only those process components and acts necessary to understand the embodiments of the present disclosure are described in detail below. A person of ordinary skill in the art will understand that some process components (e.g., pipelines, pumps, line filters, valves, temperature detectors, pressure detectors, and the like) are not described herein but that using various conventional process components and acts would be in accord with the present disclosure. The drawings accompanying the present application are for illustrative purposes only, and are not meant to be actual views of any particular material, device, or system.

Figure 1A:
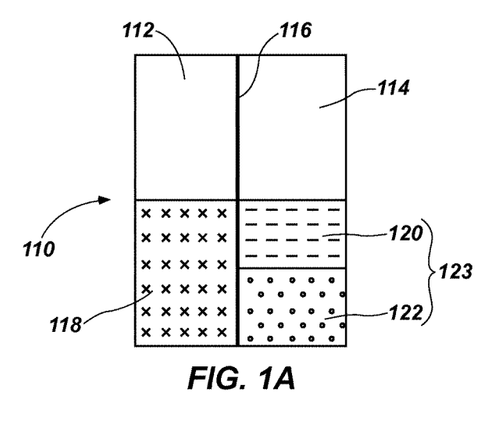
FIGS. 1A-1F are schematic drawings illustrating different process stages and structures for a method of treating a liquid, in accordance with an embodiment of the present disclosure.

One embodiment of the present disclosure will now be described with reference to FIGS. 1A-1F, which schematically illustrate different stages of a method of treating a liquid to purify or concentrate at least one of a solute and a solvent using an SHS. Referring to FIG. 1A, a feed liquid 118 may be provided to a first chamber 112 of a forward osmosis device 110. The feed liquid 118 may be a solution of a solvent (e.g., water, organic solvents such as alcohols, or combinations thereof) and at least one solute. The at least one solute may be at least one of a homogenous material and a heterogeneous material. Non-limiting examples of homogenous materials include inorganic materials (e.g., water soluble minerals, water soluble compounds such as salts), organic materials (e.g., pharmaceuticals, plasticizers, solvents, industrial chemicals, and organics found in produced water), and inorganic/organic hybrid materials (e.g., coordination complexes, and organometallic complexes such as dimethyl mercury). Non-limiting examples of heterogeneous materials include algae, microbes, small particulate matter, undissolved sewage material, nanoparticles, polymers, and food product solution materials, such as fruit juices and milk solutions. In one embodiment, the feed liquid 118 is water that includes the at least one solute. As used herein, the term "solution" means and includes a solution of the solute in the solvent, a suspension of the solute in the solvent, an emulsion of the solute in the solvent, or combinations thereof. Since a person of ordinary skill in the art will recognize whether a particular reference describes a solution, a suspension, an emulsion or a combination thereof from the context, for the purposes of readability and claiming the invention, the term "solution" means a solution, a suspension, an emulsion, or a combination thereof. The at least one solute may, undesirably, be present in the feed liquid 118 as a contaminant or impurity of the solvent (e.g., where it is desired to purify or concentrate the at least one solvent of the feed liquid 118). Alternatively, the at least one solvent may be present in the feed liquid 118 as a contaminant or impurity of the solute (e.g., where it is desired to purify or concentrate the at least one solute of the feed liquid 118). The feed liquid 118 may be a liquid stream in which a dilute solution of the solute is available, but a concentrated solution of the solute is commercially desired. By way of non-limiting example, the feed liquid 118 may include an aqueous saline solution, ocean water, brine, brackish water, mineralized water, industrial waste water, produced water, mining waste (e.g., a potash solution, a lithium salt solution), a food product solution (e.g., a fruit juice solution, milk solution), an acid solution, a base solution, a synthetic fermentation broth, algal growth media, a microbial solution, landfill leachate, a radioactive material solution, a toxic material solution, or combinations thereof. In at least some embodiments, the feed liquid 118 includes ocean water.

A hydrophobic form 120 of an SHS and a secondary solvent 122 may be provided to a second chamber 114 of the forward osmosis device 110 to form a multiple-phase draw solution 123. The second chamber 114 may be separated from the first chamber 112 by a semi-permeable membrane 116. The feed liquid 118 may be in contact with a first side of the semi-permeable membrane 116 and the multiple-phase draw solution 123 may be in contact with a second side of the semi-permeable membrane 116. The secondary solvent 122 may be any liquid that is insoluble with the hydrophobic form 120 of the SHS and that does not react with, break down, absorb, or impair the SHS in an unintended way. By way of non-limiting example, the secondary solvent 122 may be water, an alcohol (e.g., methanol, ethanol, propanol, butanol, hexanol, octanol, or combinations thereof), or combinations thereof. The secondary solvent 122 may, optionally, include materials to assist with converting the SHS from the hydrophobic form 120 to a hydrophilic form. Optionally, the secondary solvent 122 may be substantially similar to the at least one solvent of the feed liquid 118 (e.g., if the at least one solvent is water, the secondary solvent 122 may be water). In at least some embodiments, the secondary solvent 122 includes water.

In the hydrophobic form 120, the SHS may include at least one of an amine compound, an amidine compound, and a guanidine compound that is substantially insoluble with the secondary solvent 122 and the solvent of the feed liquid 118. The SHS may be tolerant of water. The general structure of each of an amine compound, an amidine compound, and a guanidine compound is, respectively, shown below:

(Amine)   (Amidine)   (Guanidine)

where $R^1$, $R^2$, $R^3$, $R^4$, and $R^5$ are independently hydrogen; a substituted or unsubstituted alkyl group (i.e., linear, branched, or cyclic) containing from 1 carbon atom to 10 carbon atoms; a substituted or unsubstituted $C_nSi_m$ group where n and m are independently an integer from 0 to 10 and n+m is an integer from 1 to 10; and a substituted or unsubstituted aryl group or heteroaryl group that may contain at least one {—Si($R^6$)$_2$—O—} where $R^6$ is a substituted or unsubstituted alkyl, aryl, heteroaryl, or alkoxy group. If a group is substituted, the substituent may be an alkyl, alkenyl, alkynl, alky halide, aryl, aryl halide, heteroaryl, non-aromatic ring, Si(alkyl)$_3$, Si(alkoxy)$_3$, alkoxy, amino, ester, amide, thioether, alkylcarbonate, or thioester group. Optionally, two or more of the $R^1$, $R^2$, $R^3$, $R^4$, and $R^5$ groups may form a ring structure (e.g., an alicylic group, or an aryl group) with each other.

The at least one of the amine compound, the amidine compound, and the guanidine compound may have a nitrogen atom to carbon atom ratio of from about 1:2 to about 1:15. If the hydrophobic form 120 of the SHS includes at least one amine compound, the at least one amine compound may be a tertiary amine that may be fully saturated at the nitrogen position. The at least one amine compound may be linear, cyclic, or branched and may include a single nitrogen atom or multiple nitrogen atoms. The at least one amine compound may be a monoamine compound (i.e., a compound including one amino group) or may a polyamine compound (i.e., a compound including two or more amino groups). In at least some embodiments, the at least one amine compound has as one nitrogen atom and less than or equal to eight carbon atoms, which provides a SHS having low volatility and low back diffusion through the semi-permeable membrane. Examples of amine compounds include, but are not limited to, cyclohexyldimethylamine, 1-butylpyrrolidine, 1-ethylpiperidine, N,N-diethylcyclohexylamine, triethylamine, N,N-dibutylmethylamine, 2-ethylhexyl-N,N-dimethylamine, N-benzyldimethylamine, N,N-dimethyl-2-phenylethanamine, N,N-dimethyl-3-phenylpropanamine, N-methyldipropylamine, N-butyldiethylamine, N-butyldimethylamine, N,N-dimethylpentylamine, N-heptyldimethylamine, N,N-dimethyloctylamine, N,N-dimethylnonanamine, N-decyldimethylamine and N-hexyldimethylamine. Examples of amidine compounds include, but are not limited to, N,N,N'-tripropylbutanamidine, N,N,N'-tributylpentanamidine, and 1,8-diazabicyclo[5.4.0]undec-7-ene (DBU). If DBU is used as the amine compound, an equal volume of an alcohol may be with the DBU. Examples of guanidine compounds include, but are not limited to, 1,1,3,3-tetramethyl-2-phenylguanidine, 2-(2-fluorophenyl)-1,1,3,3-tetramethylguanidine, 1,1,3,3-tetraethyl-2-hexylguanidine, 2-butyl-1,1,3,3-tetraethylguanidine, 2-hexyl-1,1,3,3-tetramethylguanidine, or combinations thereof. In at least some embodiments, the hydrophobic form 120 of the SHS includes cyclohexyldimethylamine, which has the structure:

The SHS are commercially available from numerous sources, such as from Sigma-Aldrich Company (St. Louis, Mo.). The SHS may be purchased at high purities, such as greater than 99% pure, at a cost comparable to the cost of conventional draw solutes.

Figure 1B:
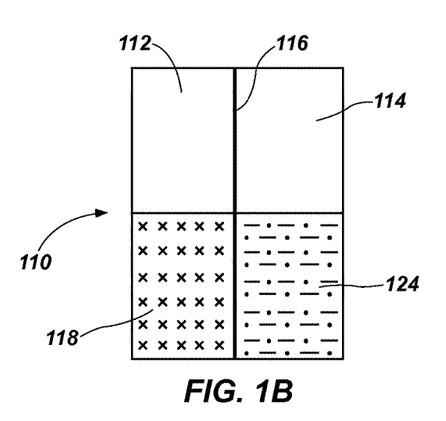

Referring next to FIG. 1B, the multiple-phase draw solution 123 (FIG. 1A) may be subjected to a non-reactive gas, such as at least one of carbon dioxide ($CO_2$), carbon disulfide ($CS_2$), and carbonyl sulfide (COS), to switch or convert the hydrophobic form 120 (FIG. 1A) of the SHS to a hydrophilic form of the SHS and form a single-phase draw solution 124 including the secondary solvent 122 (not shown) and at least one of an aminium salt, an amidinium salt, and an guanidinium salt depending on the compound used as the SHS. In one embodiment, the multiple-phase draw solution 123 is exposed to $CO_2$ to change the SHS from the hydrophobic form 120 to the hydrophilic form. The $CO_2$, $CS_2$, or COS may be a gas and flowed through the multiple-phase draw solution 123, such as by flowing the $CO_2$, $CS_2$, or COS through an aerator in the multiple-phase draw solution 123. As used herein, the term "aminium salt" means and includes an aminium cation and an anionic counterion and has a neutral charge. By way of non-limiting example, where the multiple-phase draw solution 123 (FIG. 1A) includes at least one amine compound and water, adding or introducing $CO_2$ to the multiple-phase draw solution 123 (FIG. 1A) may convert the at least one amine compound (e.g., the hydrophobic form 120 of the SHS) into an aminium bicarbonate (e.g., the hydrophilic form of the SHS) according to the following reversible reaction:

(1)

where $R^1$, $R^2$, and $R^3$ are as defined above. As used herein, the term "amidinium salt" means and includes an amidinium cation and an anionic counterion and has a neutral charge. By way of non-limiting example, where the multiple-phase draw solution 123 (FIG. 1A) includes at least one amidine compound (e.g., the hydrophobic form 120 of the SHS) and water, adding or introducing $CO_2$ may yield a single-phase draw solution 124 including an amidinium bicarbonate (e.g., the hydrophilic form of the SHS) according to the following reversible reaction:

(2)

where $R^1$, $R^2$, $R^3$, and $R^4$ are as defined above. As used herein, the term "guanidinium salt" means and includes a guanidinium cation and an anionic counterion and has a neutral charge. By way of non-limiting example, where the multiple-phase draw solution 123 (FIG. 1A) includes at least one guanidine compound (e.g., the hydrophobic form 120 of the SHS) and water, adding or introducing $CO_2$ may yield a single-phase draw solution 124 including an guanidinium bicarbonate (e.g., the hydrophilic form of the SHS) according to the following reversible reaction:

(3)

where $R^1$, $R^2$, $R^3$, $R^4$ and $R^5$ are as defined above.

As an additional non-limiting example, where the multiple-phase draw solution 123 (FIG. 1A) includes at least one amine compound (e.g., the hydrophobic form 120 of the SHS) and alcohol, adding or introducing $CO_2$ to the multiple-phase draw solution 123 (FIG. 1A) may convert the at least one amine compound into an aminium alkyl carbonate (e.g., the hydrophilic form of the SHS) according to the following reversible reaction:

(4)

where X is a substituted or unsubstituted alkyl, alkenyl, alkynyl, aryl, silyl, or siloxyl, and may be linear, branched, or cyclic. Where the multiple-phase draw solution 123 (FIG. 1A) includes an amidine compound (e.g., the hydrophobic form 120 of the SHS) and alcohol, adding or introducing $CO_2$ may yield a single-phase draw solution 124 including amidinium alkyl carbonate (e.g., the hydrophilic form of the SHS) according to the following reversible reaction:

(5)

where $R^1$, $R^2$, $R^3$, $R^4$, and X are as defined above. Where the multiple-phase draw solution 123 (FIG. 1A) includes a guanidine compound (e.g., the hydrophobic form 120 of the SHS) and alcohol, adding or introducing $CO_2$ may yield a single-phase draw solution 124 including guanidinium alkyl carbonate (e.g., the hydrophilic form of the SHS) according to the following reversible reaction:

(6)

where $R^1$, $R^2$, $R^3$, $R^4$, $R^5$, and X are as defined above.

In at least some embodiments, the multiple-phase draw solution 123 (FIG. 1A) includes cyclohexyldimethylamine and water, and is exposed to $CO_2$ to form a single-phase draw solution 124 including cyclohexyldimethylaminium bicarbonate according to the following reversible reaction:

(7)

The cyclohexyldimethylamine is immiscible in water and the cyclohexyldimethylaminium bicarbonate is miscible in water.

In one or more embodiments, exposing the multiple-phase draw solution 123 (FIG. 1A) to $CO_2$ may form an aminium, amidinium, and/or guanidinium salt including a carbonate ($CO_3^{2-}$) anionic counterion (e.g., an aminium carbonate, an amidinium carbonate, a guanidinium carbonate).

While the combination of FIGS. 1A and 1B illustrate formation of the multiple-phase draw solution 123 (FIG. 1A) and the single-phase draw solution 124 (FIG. 1B) within the second chamber 114 of the forward osmosis device 110, each may be formed outside the forward osmosis device 110 and directed to the second chamber 114. For example, the multiple-phase draw solution 123 may be formed in at least one separate vessel (not shown), the multiple-phase draw solution 123 may be exposed to at least one of $CO_2$, $CS_2$, and COS to form the single-phase draw solution 124 in the at least one separate vessel, and the single-phase draw solution 124 may be directed from the at least one separate vessel into the second chamber 114 of the forward osmosis device 110.

Referring to FIG. 1B, the single-phase draw solution 124 may include a concentration of the hydrophilic form of the SHS that is greater than a total solute concentration of the feed liquid 118. The difference in concentration between the single-phase draw solution 124 and the feed liquid 118 creates an osmotic pressure differential across the semi-permeable membrane 116 to draw the solvent of the feed liquid 118 toward the single-phase draw solution 124 by forward osmosis (i.e., the general tendency of a solvent, such as water, to move from a less concentrated environment to a more concentrated environment). The single-phase draw solution 124 may include a concentration of the hydrophilic form of the SHS within a range of from a lowest effective concentration of the hydrophilic form of the SHS (i.e., to facilitate a draw on the solvent of the feed liquid 118) to a solubility limit of the hydrophilic form of the SHS for the single-phase draw solution 124. By way of non-limiting example, the concentration of the hydrophilic form of the SHS for the single-phase draw solution may be within a range of from about 0.5 molal to about 20.0 molal, such as from about 1.0 molal to about 14.0 molal. In at least some embodiments, the single-phase draw solution 124 has a concentration of the hydrophilic form of the SHS of about 7.6 molal. The concentration of the hydrophilic form of the SHS in the single-phase draw solution 124 may be controlled as desired by adjusting an amount of the hydrophobic form of the SHS in the secondary solvent.

While FIG. 1B shows the feed liquid 118 and the single-phase draw solution 124 as being substantially stagnant, at least one of the single-phase draw solution 124 and the feed liquid 118 may be flowed or passed through the forward osmosis device 110. For example, the feed liquid 118 may be flowed or passed through the first chamber 112 of the forward osmosis device 110, and the single-phase draw solution 124 may be flowed or passed through the second chamber 114 of the forward osmosis device 110. The feed liquid 118 and the single-phase draw solution 124 may be flowed or passed through the forward osmosis device 110 in the same direction (i.e., concurrent flow) or in opposite directions (i.e., countercurrent flow). In at least one embodiment, the feed liquid 118 and the single-phase draw solution 124 are flowed through the forward osmosis device 110 in opposite directions.

Figure 1C:
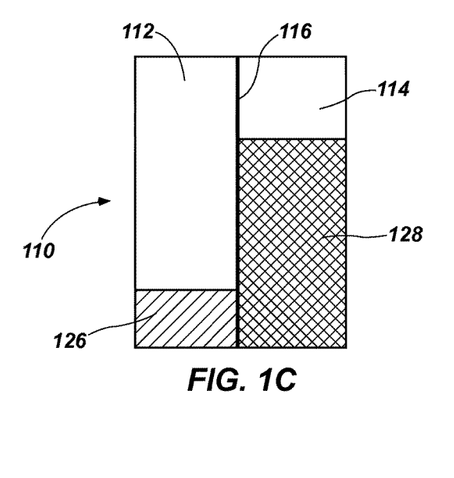

Referring to FIG. 1C, as the solvent of the feed liquid 118 (FIG. 1B) is drawn toward the single-phase draw solution 124, at least a portion of the solvent may osmose or diffuse through the semi-permeable membrane 116 to form a solute concentrate 126 in the first chamber 112 and a diluted single-phase draw solution 128 in the second chamber 114, where the diluted single-phase draw solution 128 includes the at least a portion of the solvent. The semi-permeable membrane 116 may be any conventional membrane configured to facilitate the diffusion of the solvent from the first chamber 112 into the second chamber 114, while substantially preventing the diffusion or passage of the at least one solute from the first chamber 112 into the second chamber 114. The semi-permeable membrane 116 may also substantially prevent the diffusion or passage of the hydrophilic and hydrophobic forms of the SHS from the second chamber 114 into the first chamber 112. Suitable semi-permeable membranes 116 are commercially available from numerous sources including, but not limited to, Hydration Technology Innovations (Scottsdale, Ariz.) under at least the HYDROPACK®, LIFEPACK®, SEAPACK®, X-PACK, HYDROWELL®, and EXPEDITION™ tradenames. The solute concentrate 126 may be disposed of or utilized as desired. The diluted single-phase draw solution 128 may be further processed, as described below.

Figure 1D:
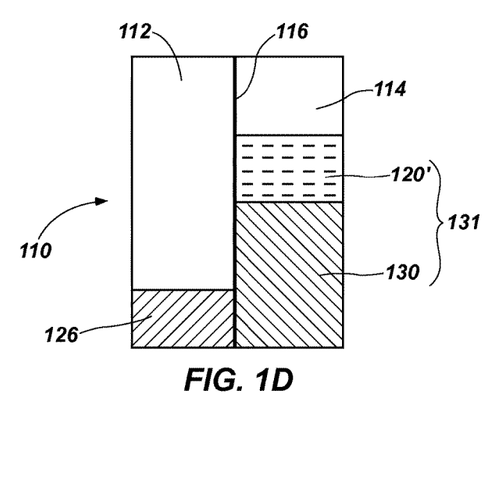

Referring next to FIG. 1D, the diluted single-phase draw solution 128 (FIG. 1C) may be subjected to a change of reaction conditions facilitating the release of at least one of $CO_2$, $CS_2$, and COS from the diluted single-phase draw solution 128 to convert the hydrophilic form of the SHS back into the hydrophobic form 120' and produce a multiple-phase solution 131 including the hydrophobic form 120' of the SHS and a liquid product 130. By way of non-limiting example, the change of reaction conditions may be effectuated by exposing the diluted single-phase draw solution 128 (FIG. 1C) to at least one of heat, reduced pressure, and a non-reactive gas (e.g., $N_2$, argon, air) at least substantially free of $CO_2$, $CS_2$, and COS. Where the change of reaction conditions facilitates the release of $CO_2$, the hydrophilic form of the SHS may be converted to the hydrophobic form 120' of the SHS according to a reverse reaction of at least one of reactions (1) through (7) above. The liquid product 130 may include a mixture of the solvent, the secondary solvent 122, and a trace amount of at least one of the hydrophobic form 120' and the hydrophilic form of the SHS.

While FIG. 1D illustrates formation of the multiple-phase solution 131 within the second chamber 114 of the forward osmosis device 110, the multiple-phase solution 131 may be formed outside the forward osmosis device 110. For example, the diluted single-phase draw solution 128 (FIG. 1C) may be directed out of the second chamber 114 of the forward osmosis device 110 and into at least one separate vessel (not shown) where the diluted single-phase draw solution 128 (FIG. 1C) may be exposed to the at least one of heat, reduced pressure, and non-reactive gas at least substantially free of $CO_2$, $CS_2$, and COS to form the multiple-phase solution 131.

Following the formation of the multiple-phase solution 131, the hydrophobic form 120' of the SHS and the liquid product 130 may be separated, such as by mechanical separation. Any conventional techniques of mechanical separation capable of substantially separating the hydrophobic form 120' of the SHS and the liquid product 130 may be used, such as one or more of decanting, filtering, and centrifuging. Upon separation, the hydrophobic form 120' of the SHS may be directed or recycled to the second chamber 114 of the forward osmosis device 110 (or a separate vessel) for use in repeating the process described above. The liquid product 130 may be further processed, as described below. However, if the feed liquid 118 is being treated to purify or concentrate the at least one solute (e.g., to form the solute concentrate 126), further processing of the liquid product 130 may, optionally, be omitted.

Figure 1E:
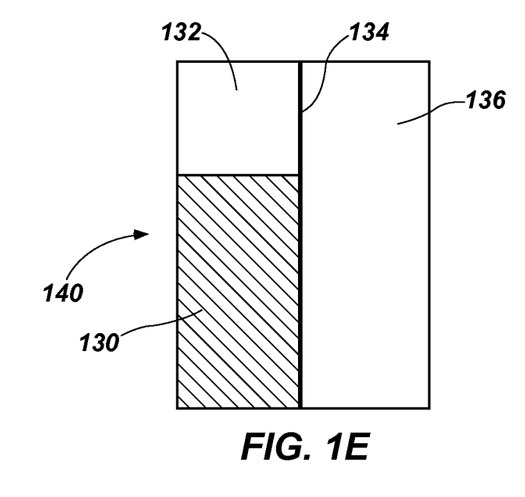

Referring to FIG. 1E, the liquid product 130 may be directed into a first chamber 132 of a filtration device 140. The first chamber 132 may be separated from a second chamber 136 by a semi-permeable membrane 134. The second chamber 136 may be substantially empty. The semi-permeable membrane 134 may be any conventional membrane configured to facilitate a pressure assisted diffusion of the solvent and the secondary solvent 122 (FIG. 1A) of the liquid product 130 from the first chamber 132 into the second chamber 136 of the filtration device 140, while substantially preventing diffusion or passage of hydrophobic and hydrophilic forms of the SHS from the first chamber 132 into the second chamber 136 of the filtration device 140. By way of non-limiting example, the semi-permeable membrane 134 may include at least one reverse osmosis membrane, commercially available from numerous sources, such as from Hydration Technology Innovations (Scottsdale, Ariz.).

Figure 1F:
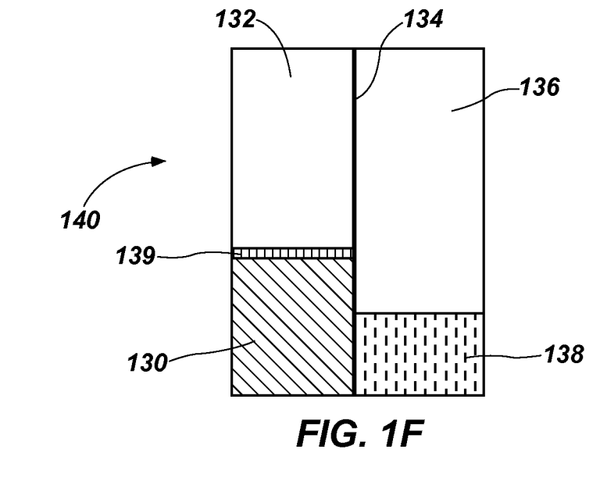

Referring next to FIG. 1F, pressure may be applied to the liquid product 130 within the first chamber 132 of the filtration device 140 to force at least a portion of each of the solvent and the secondary solvent 122 (FIG. 1A) through the semi-permeable membrane 134 and into the second chamber 136 to form a purified liquid product 138. A separated SHS 139 including at least one of the hydrophilic form and the hydrophobic form 120' of the SHS may be temporarily retained within the first chamber 132 of the filtration device 140. The purified liquid product 138 may be utilized as desired. The separated SHS 139 may be directed or recycled into the second chamber 114 of the forward osmosis device 110 (or a separate vessel) for use in repeating the process described above.

Advantageously, at least a solubility limit of at least the hydrophobic form of the SHS in the liquid product 130 may reduce or prevent concentration polarization problems frequently associated with using pressurized filtration (e.g., reverse osmosis) to purify liquids. As used herein, the term "concentration polarization" means and includes a phenomenon where the less than immediate dilution of solute left behind as a liquid (e.g., water) diffusing through a semi-permeable membrane creates an increased concentration of solute in a portion of the liquid adjacent the semi-permeable membrane relative to a concentration of solute in a remainder of the liquid. Concentration polarization may lead to one or more of reduced liquid transport or flux through the semi-permeable membrane, increased solute leakage through the semi-permeable membrane, and increased pressure demands to osmose the liquid through the semi-permeable membrane. As the hydrophobic form of the SHS may have a substantially lower solubility limit in the liquid product 130 than a conventional draw solute (e.g., NaCl, KCl, $MgCl_2$, $CaCl_2$, etc.), the hydrophobic form of the SHS may phase separate from the liquid product 130 before a conventional draw solute would, generating relatively reduced or no concentration polarization in the liquid product 130. By way of non-limiting example, the hydrophobic form of the SHS may have a solubility limit in the liquid product 130 of less than or equal to about 0.5 Osm/kg, such as less than or equal to about 0.3 Osm/kg, or less than or equal to about 0.15 Osm/kg, or less than or equal to about 0.0035 Osm/kg, whereas the solubility limit of conventional draw solutes may be much greater (e.g., NaCl: about 12.3 Osm/kg, KCl: about 9.2 Osm/kg, $MgCl_2$: about 17.12 Osm/kg, $CaCl_2$: about 20.1 Osm/kg, etc.).

While the combination of FIGS. 1E and 1F illustrate producing the purified liquid product 138 through pressure-assisted filtration, the purified liquid product 138 may be produced through any conventional methods or techniques capable of removing trace amounts of the hydrophobic and hydrophilic forms of the SHS from the processed liquid product 130. By way of non-limiting example, the purified liquid product 138 may be produced by subjecting the liquid product 130 to at least one of adsorption, distillation, electrodialysis, and evaporation.

Figure 2A:
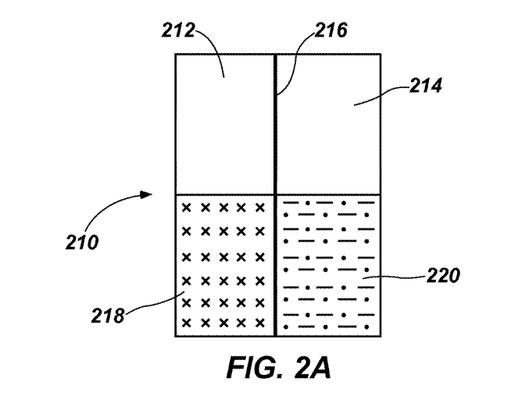
FIGS. 2A-2D are schematic drawings illustrating different process stages and structures for another method of treating a liquid, in accordance with an embodiment of the present disclosure.

Another embodiment of the present disclosure will now be described with reference to FIGS. 2A-2D, which schematically illustrate a method of treating a liquid including at least one organic solute and at least one inorganic solute using an SHS. Referring to FIG. 2A, a feed liquid 218 may be provided into a first chamber 212 of a forward osmosis device 210. The feed liquid 218 may include a solvent (e.g., water, organic solvents such as alcohols, or combinations thereof), at least one organic solute (e.g., a pharmaceutical, oil), and at least one inorganic solute (e.g., a mineral, a salt such as NaCl, KCl).

A single-phase draw solution 220 including a hydrophilic form of an SHS and a secondary solvent (e.g., water, alcohol, or combinations thereof) may be provided in a second chamber 214 of the forward osmosis device 210. The second chamber 214 may be separated from the first chamber 212 by a semi-permeable membrane 216. The feed liquid 218 may be in contact with a first side of the semi-permeable membrane 216 and the single-phase draw solution 220 may be in contact with a second side of the semi-permeable membrane 216. The hydrophilic form of the SHS may include at least one of an aminium salt, an amidinium salt, and a guanidinium salt. The hydrophilic form of the SHS may be formed within or outside of the second chamber 214 in a manner substantially similar to that described above for the single-phase draw solution 124. For example, a hydrophobic form (not shown) of the SHS including at least one of an amine compound, an amidine compound, and a guanidine compound may be combined with at least one water and alcohol, and exposed to one or more of $CO_2$, $CS_2$, and COS to form the single-phase draw solution 220. Where the hydrophobic form of the SHS is exposed to $CO_2$, the single-phase draw solution 220 may be formed according to at least one of reactions (1) through (7) above.

The single-phase draw solution 220 may have a concentration of the hydrophilic form of the SHS that is greater than a total solute (i.e., combined organic and inorganic solutes) concentration of the feed liquid 218. The concentration difference between the feed liquid 218 and the single-phase draw solution 220 creates an osmotic pressure differential across the semi-permeable membrane 216 to draw the solvent of the feed liquid 218 toward the single-phase draw solution 220 by forward osmosis. The single-phase draw solution 220 may have a concentration of the hydrophilic form of the SHS within a range of from a lowest effective concentration of the hydrophilic form of the SHS (i.e., to facilitate a draw on the solvent of the feed liquid 218) to a solubility limit of the hydrophilic form of the SHS for the single-phase draw solution 220. By way of non-limiting example, the concentration of the hydrophilic form of the SHS for the single-phase draw solution may be within a range of from about 0.5 molal to about 20.0 molal, such as from about 1.0 molal to about 14.0 molal. In at least some embodiments, the single-phase draw solution 124 has a concentration of the hydrophilic form of the SHS of about 7.6 molal. The concentration of the hydrophilic form of the SHS may be controlled as desired at least by adjusting an amount of at least one of the hydrophobic form of the SHS and the secondary solvent (e.g., water, alcohol) used to form the single-phase draw solution.

Figure 2B:
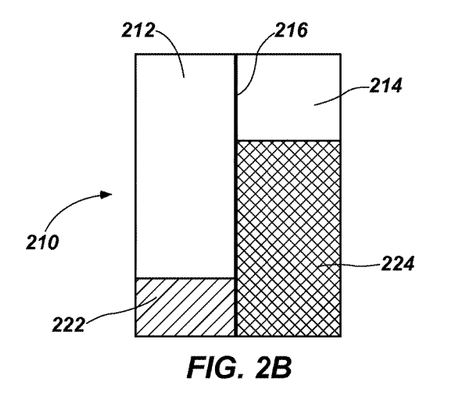

Referring next to FIG. 2B, as the solvent of the feed liquid 218 (FIG. 2A) is drawn toward the single-phase draw solution 220, at least a portion of the solvent and the at least one organic solute may diffuse or osmose through the semi-permeable membrane 216 to form an inorganic solute concentrate 222 in the first chamber 212 and a diluted single-phase draw solution 224 in the second chamber 214, the diluted single-phase draw solution 224 including the at least a portion of the solvent and the at least one organic solute. The semi-permeable membrane 216 may be any conventional membrane configured to facilitate the diffusion of the solvent and the at least one organic solute from the first chamber 212 into the second chamber 214, while substantially preventing the diffusion or passage of the at least one inorganic solute from the first chamber 212 into the second chamber 214. The semi-permeable membrane 216 may also substantially prevent the diffusion or passage of the hydrophilic form of the SHS from the second chamber 214 into the first chamber 212. The inorganic solute concentrate 222, which may include the inorganic solute and a remaining portion of the solvent and the organic solute may be further processed or disposed of as desired. The diluted single-phase draw solution 224 may be further processed, as described below.

Figure 2C:
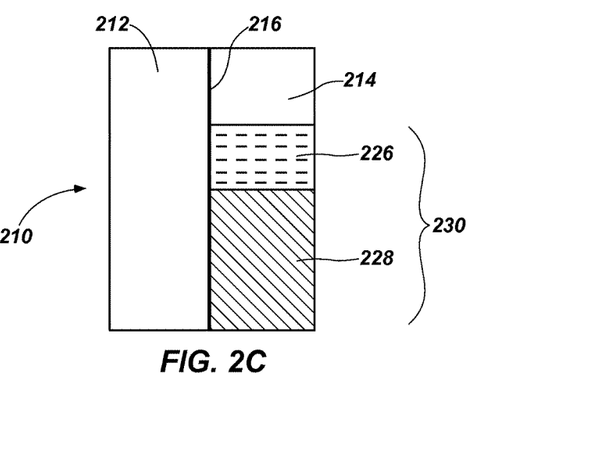

Referring to FIG. 2C, the diluted single-phase draw solution 224 (FIG. 2B) may be subjected to a change of reaction conditions facilitating the release of at least one of $CO_2$, $CS_2$, and COS from the diluted single-phase draw solution 224 to convert the hydrophilic form of the SHS into the hydrophobic form of the SHS and form a first multiple-phase solution 230 including a liquid product 228 and a concentrated draw solution 226. By way of non-limiting example, the change of reaction conditions may be effectuated by exposing the diluted single-phase draw solution 224 (FIG. 2B) to at least one of heat, reduced pressure, and a non-reactive gas (e.g., $N_2$, argon, air) at least substantially free of $CO_2$, $CS_2$, and COS. Where the change of reaction conditions facilitates the release of $CO_2$, the hydrophilic form of the SHS may be converted to the hydrophobic form of the SHS according to a reverse reaction of at least one of reactions (1) through (7) above. The concentrated draw solution 226 may include a mixture of the hydrophobic form of the SHS and the at least one organic solute from the feed liquid 218 (FIG. 1A). The liquid product 228 may include a mixture of the solvent and a trace amount of at least one of the hydrophobic form and the hydrophilic form of the SHS. The liquid product 228 may be separated from the concentrated draw solution 226 and further processed in a manner substantially similar to that described above for the liquid product 130. Upon separating the liquid product 228 and the concentrated draw solution 226, the concentrated draw solution 226 may be further processed, as described below.

Figure 2D:
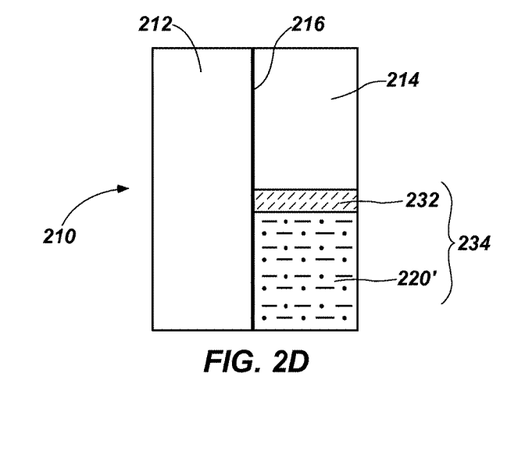

Referring to next FIG. 2D, the concentrated draw solution 226 may be exposed to at least one of $CO_2$, $CS_2$, and COS, and at least one of water and alcohol to form a second multiple-phase solution 234 including the single-phase draw solution 220' (i.e., a solution of the hydrophilic form of the SHS and at least one of alcohol and water) and an organic concentrate 232. The single-phase draw solution 220' and the organic concentrate 232 may be separated, such as by mechanical separation. Conventional techniques of mechanical separation configured to substantially separate the hydrophilic form of the SHS and the organic concentrate 232 may be used, such as one or more of decanting, filtering, and centrifuging. Upon separation, the single-phase draw solution 220' may be directed or recycled to the second chamber 214 of the forward osmosis device 210 (or a separate vessel) for use in repeating the process described above. Optionally, at least one of water and alcohol may be added or introduced to the single-phase draw solution 220' before or after the single-phase draw solution 220' is received in the second chamber 214 of the forward osmosis device 210. The organic concentrate 232 may be utilized or disposed of as desired.

Figure 3:
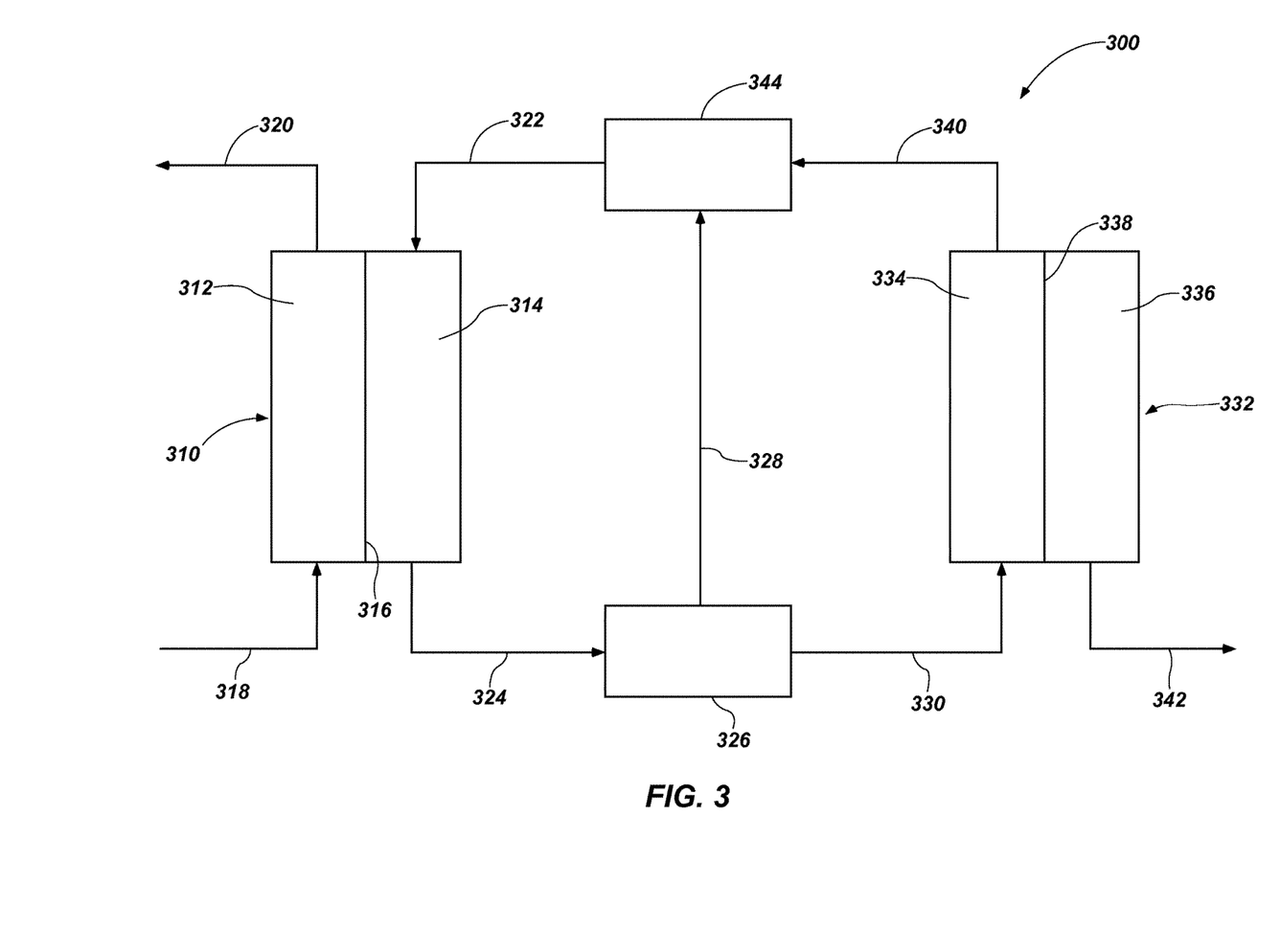
FIG. 3 is a schematic drawing of a liquid treatment system, in accordance with an embodiment of the present disclosure.

Another embodiment of the present disclosure will now be described with reference to FIG. 3, which schematically illustrates a liquid treatment system 300. As shown in FIG. 3, the liquid treatment system 300 may include a forward osmosis device 310, a first solvent switching area 326, a filtration device 332, and a second solvent switching area 344. The forward osmosis device 310 receives a feed liquid stream 318 in a first chamber 312 and a draw solution stream 322 in a second chamber 314. Within the forward osmosis device 310, an osmotic pressure gradient extending through a semi-permeable membrane 316 facilitates diffusion or transfer of solvent from the feed liquid stream 318 into the draw solution stream 322 to form each of a solute concentrate stream 320 and a diluted draw solution stream 324. The solute concentrate stream 320 may exit the first chamber 312 of the forward osmosis device 310 and may be utilized or disposed of as desired. The diluted draw solution stream 324 may be directed out of the second chamber 314 of the forward osmosis device 310 and into the first solvent switching area 326.

The first solvent switching area 326 facilitates the conversion of the diluted draw solution stream 324 into a first concentrated draw solution stream 328 and a liquid product stream 330. The first solvent switching area 326 may include at least one conventional device or conventional apparatus configured to expose the diluted draw solution stream 324 to one or more of heat, reduced pressure, and a non-reactive gas (e.g., $N_2$, argon, air) to form an multiple-phase liquid solution. By way of non-limiting example, the first solvent switching area 326 may include a tank (not shown) equipped with a gas contactor (not shown). The first solvent switching area 326 may also include a conventional separation device (e.g., a decanter, a filter, a centrifuge) configured to separate liquid phases of the multiple-phase liquid solution to form the first concentrated draw solution stream 328 and the liquid product stream 330. The first concentrated draw solution stream 328 and the liquid product stream 330 may each be directed out of the first solvent switching area 326 for further processing as described below.

Upon exiting the first solvent switching area 326, the liquid product stream 330 may be directed into a first chamber 334 of the filtration device 332. Within the filtration device 332, pressure may be applied to the liquid product stream 330 to drive a desired solvent therein through a semi-permeable membrane 338 and into a second chamber 336 to form each of a second concentrated draw solution stream 340 and a purified liquid product stream 342. In at least some embodiments, the semi-permeable membrane 338 is a reverse osmosis membrane. The purified liquid product stream 342 may exit the second chamber 336 of the filtration device 332 and may be utilized as desired. The second concentrated draw solution stream 340 may be directed out of the first chamber 334 of the filtration device 332 and into the second solvent switching area 344.

The second solvent switching area 344 may receive each of the first concentrated draw solution stream 328 and the second concentrated draw solution stream 340 and may produce the draw solution stream 322. The second solvent switching area 344 may include at least one conventional device or conventional apparatus configured and operated to expose the first concentrated draw solution stream 328 and the second concentrated draw solution stream 340 (e.g., together or separately) to one or more of $CO_2$, $CS_2$, and COS, and at least one of water and alcohol. By way of non-limiting example, the second solvent switching area 344 may include a mixer (not shown) in communication with a tank (not shown) including at least one gas contactor (not shown). Optionally, the second solvent switching area 344 may also include a conventional separation device (e.g., a filter, a centrifuge) configured and operated to separate an organic concentrate phase and a draw solution phase of a multi-phase solution. The draw solution stream 322 may be directed out of the second solvent switching area 344 and into the second chamber 314 of the forward osmosis device 310 to facilitate another pass through the liquid treatment system 300.

The methods and systems of the present disclosure advantageously reduce energy demands as compared to conventional liquid treatment methods and systems for the purification or concentration of at least one of a solvent and a solute, including conventional methods and systems utilizing a combination of forward and reverse osmosis. For example, during reverse osmosis, conventional methods and systems require application of significant pressure to overcome the osmotic pressure of the draw solute and separate the solvent therefrom. Conversely, the methods and systems of the present disclosure enable a majority of the SHS (i.e., used as a draw solute) to be easily removed without using reverse osmosis by a simple change of reaction conditions (e.g., exposure to $CO_2$ to perform a SHS hydrophilicity switch) followed by separation. When needed, reverse osmosis may be used to separate trace amounts of SHS from the solvent, facilitating the use of lower pressures relative to conventional technologies. Additionally, as described above, due at least to solubility limitations, SHSs generate little to no concentration polarization during pressure driven filtration (e.g., reverse osmosis), further reducing pressure requirements as compared to liquid treatment systems using conventional draw solutes.

The methods and systems of the present disclosure are favorable as compared to conventional liquid treatment methods and systems utilizing an ammonium ($NH_4^+$) salt (e.g., ammonium carbamate, ammonium bicarbonate, ammonium carbonate) as a draw solute at least because SHSs are safer and reduce operational costs. Following forward osmosis, conventional methods and systems using an ammonium salt generally decompose the draw solute into gaseous ammonia and carbon dioxide. The toxicity and reactivity of gaseous ammonia makes such methods and systems difficult, dangerous, and expensive. In contrast, SHSs are liquids that generally exhibit relatively lower toxicity and volatility, enabling the methods and systems of the present disclosure to be less complicated, less dangerous, and more affordable.

The methods and systems of the present disclosure are also favorable at least because they enable the removal of organic molecules that may survive conventional water treatment technologies. The persistence of organic molecules in the "purified" liquid product of conventional liquid purification systems has been a growing concern for consumers and regulators.

The following examples serve to explain embodiments of the present disclosure in more detail. These examples are not to be construed as being exhaustive or exclusive as to the scope of this invention.

EXAMPLES

Example 1

Figure 4:
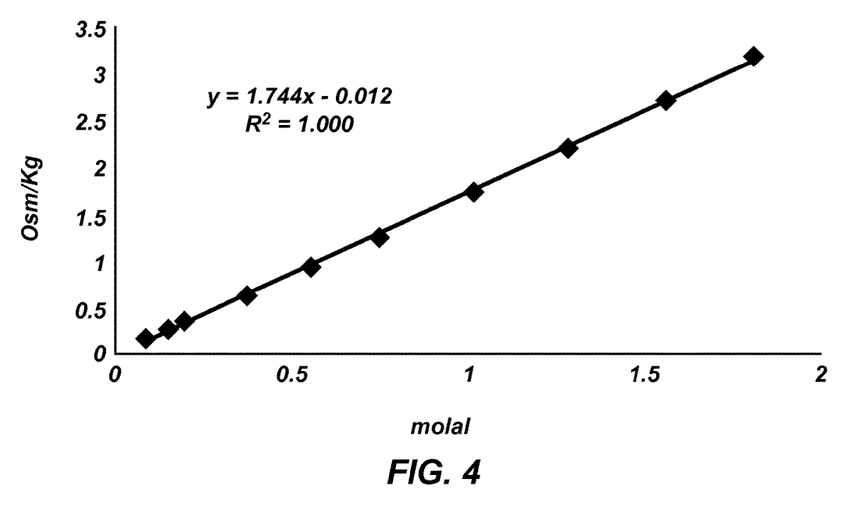
FIG. 4 is a graphical representation of the results described in Example 1.

The osmotic pressure of an aqueous solution including 59 weight percent cyclohexyldimethylaminium bicarbonate (7.6 molal) was extrapolated to be about 13.3 Osm/kg (325 atm) of osmotic pressure. By way of comparison, a simulated ocean water solution including 3.5 weight percent dissolved solids had an osmotic pressure of about 27 atm or about 1.0 Osm/Kg. This extrapolation is achieved by extending the linear relationship in osmolality dependence on the concentration of the cyclohexyldimethylaminium bicarbonate from concentrations between 0.09 and 1.81 molal. The osmolalities were found through freezing depression experiments on an osmometer. The correlation between freezing point depression, osmolality, and osmotic pressure is well established. A graphical representation of the osmolality data for of aqueous cyclohexyldimethylaminium bicarbonate solutions at different cyclohexyldimethylaminium bicarbonate concentrations is shown in FIG. 4

Example 2

Figure 5:
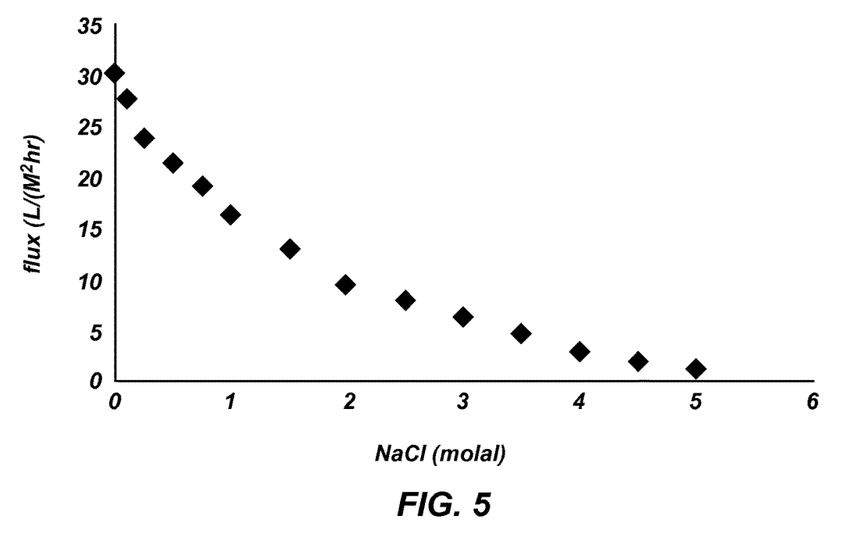
FIG. 5 is a graphical representation of the results described in Example 2.

Aqueous saline solutions including house deionized water and varied concentrations of sodium chloride were separately provided on first sides of Hydration Technology Innovations (HTI) cartridge membranes, with aqueous draw solutions having an initial concentration of 7.6 molal cyclohexyldimethylaminium bicarbonate provided on second sides of the HTI cartridge membranes. The aqueous saline solutions and the aqueous draw solutions were each maintained at a temperature of about 30° C. An osmotic pressure differential across each of the HTI cartridge membranes generated a flow of the house deionized water from the first side of each of the membranes, across each of the membranes, and to the second side of each of the membranes. During each test, flux was allowed to stabilize over a period of from about one minute to about three minutes, and flux during a subsequent ten minute period was averaged to determine the initial flux of the system. A graphical representation of flux against sodium chloride concentration is shown in FIG. 5.

Example 3

Cyclohexyldimethylamine (68.4 g) was added to deionized water (4.095) kg and stirred overnight to form a homogenous 16.7 g/L solution. This solution was nm through a RO unit containing a polyamide thin-film composite membrane. During the 4 hr experiment 3.925 kg of purified water was produced, divided into 17 samples of approximately 231 g each. The feed solution became torpid when the RO process was begun and an organic layer formed within the removal of the first 200 g of liquid. When the separation was complete the remaining feed solution and first wash of the system contained organic layers totaling 67.5 ml (59.4 g). On average the purified water contained less than 0.06 g/L cyclohexyldimethylamine measured by the GC FID and the concentration did not significantly increase or decrease during the course of the experiment. This is a 99.65% rejection rate of the dissolved cyclohexyldimethylamine.

Example 4

Toluene (95 µl, 82.5 mg) was dissolved in water (202.6 g) to which was added cyclohexyldimethylammonium bicarbonate solution (113.3 g, 7.6 mol/Kg, 0.35 mol) to form a 275 µg/ml solution of toluene. This solution was mixed for several minutes, after which sodium hydroxide (19.2 g, 0.48 mol) was added, resulting in a phase separation in to an aqueous (~296 g) and organic phase (~36 g). The organic phase represents 82% of the total cyclohexyldimethylamine in the system with 8.2 g still contained in the aqueous phase. Samples were taken from each phase and analyzed with GC-FID liquid injection method, the aqueous phase contained 110 µg/ml toluene and the organic phase contained 1,200 µg/ml toluene.

Example 5

Toluene (1.84 g) was added to cyclohexyldimethylamine (6.86 g, 54 mmol) and was completely miscible. Toluene (1.83 g) was added to 7.6 mol/Kg cyclohexyldimethylammonium bicarbonate (17.11 g, 53 mmol) and was generally immiscible. The aqueous dimethylcyclohexylammonium bicarbonate fraction contained ~0.3 wt % toluene based on quantitative $^1$H NMR.

While the present disclosure may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents. For example, elements and features disclosed in relation to one embodiment may be combined with elements and features disclosed in relation to other embodiments of the present invention.

What is claimed is:

1. A method of treating a liquid, the method comprising:
    providing a feed liquid comprising at least one solvent and at least one solute to a first side of a membrane;
    providing a single-phase draw solution comprising one or more of an amidinium salt, a guanidinium salt, and a tertiary aminium salt to a second side of the membrane;
    drawing the at least one solvent across the membrane and into the single-phase draw solution through forward osmosis to form a diluted single-phase draw solution; and
    exposing the diluted single-phase draw solution to one or more of heat, reduced pressure, and a non-reactive gas to release one or more of $CO_2$, $CS_2$, and COS from the diluted single-phase draw solution and form a multiple-phase solution comprising:
        a first liquid phase comprising the at least one solvent; and
        a second liquid phase comprising one or more of an amidine compound, a guanidine compound, and a tertiary amine compound.

2. The method of claim 1, wherein providing the feed liquid comprises providing one or more of an aqueous saline solution, ocean water, brine, brackish water, mineralized water, industrial waste water, produced water, mining waste, food product solution, acid solution, base solution, synthetic fermentation broth, algal growth media, microbial solution, landfill leachate, radioactive material solution, and toxic material solution.

3. The method of claim 1, further comprising:
    separating the first liquid phase of the multiple-phase solution from the second liquid phase of the multiple-phase solution;
    combining the separated first liquid phase with an additional amount of the at least one solvent;
    exposing the combination of the separated first liquid phase and the additional amount of the at least one solvent to one or more of additional $CO_2$, additional $CS_2$, and additional COS to reform the single-phase draw solution; and
    contacting the second side of the membrane with the reformed single-phase draw solution.

4. The method of claim 3, further comprising adjusting an amount of one or more of the separated first liquid phase and the additional amount of the at least one solvent to impart the reformed single-phase draw solution with a greater concentration of the one or more of the tertiary aminium salt, the amidinium salt, and the guanidinium salt than a total solute concentration of the feed liquid.

5. The method of claim 3, wherein the tertiary amine compound comprises a ratio of nitrogen to carbon of from about 1:2 to about 1:15.

6. The method of claim 5, wherein the tertiary amine compound comprises one nitrogen atom and less than or equal to eight carbon atoms.

7. The method of claim 1, wherein the single-phase draw solution comprises one or more of a tertiary aminium bicarbonate, a tertiary aminium carbonate, a tertiary aminium alkyl carbonate, an amidinium bicarbonate, an amidinium carbonate, an aminium alkyl carbonate, an guanidinium bicarbonate, an guanidinium carbonate, and an guanidinium alkyl carbonate.

8. The method of claim 1, further comprising separating the first liquid phase and the second liquid phase of the multiple-phase solution to form each of a first concentrated draw solution and a liquid product, wherein the first concentrated draw solution comprises the one or more of the amidine compound, the guanidine compound, and the tertiary amine compound, and wherein the liquid product comprises the at least one solvent and a trace amount of one or more of the amidine compound, the guanidine compound, and the tertiary amine compound.

9. The method of claim 8, wherein separating the first liquid phase and the second liquid phase of the multiple-phase solution comprises one or more of decanting, filtering, and centrifuging the multiple-phase solution.

10. The method of claim 8, further comprising separating the at least one solvent and the trace amount of the one or more of the amidine compound, the guanidine compound, and the tertiary amine compound to form each of a purified liquid product and a second concentrated draw solution.

11. The method of claim 10, wherein separating the at least one solvent and the trace amount of the one or more of the amidine compound, the guanidine compound, and the tertiary amine compound comprises filtering the liquid product by reverse osmosis.

12. The method of claim 10, further comprising exposing one or more of the first concentrated draw solution and the second concentrated draw solution to one or more of additional $CO_2$, additional $CS_2$, additional COS, and one or more of water and alcohol to form the single-phase draw solution.

13. The method of claim 12, further comprising separating the single-phase draw solution and at least one organic solute removed from the feed liquid.

14. A method of liquid treatment, the method comprising:
    diffusing water from a feed solution through a semi-permeable membrane and into a draw solution comprising a hydrophilic solvent and one or more of water and alcohol through forward osmosis to form a diluted draw solution, the hydrophilic solvent comprising:
        one or more of an amidinium cation, a guanidinium cation, and a tertiary aminium cation; and
        one or more of a bicarbonate anion, a carbonate anion, and an alkyl carbonate anion;
    exposing the diluted draw solution to one or more of heat, reduced pressure, and a non-reactive gas to form a first multiple-phase solution comprising a water phase and a hydrophobic solvent phase comprising a hydrophobic solvent comprising one or more of an amidine compound, a guanidinium compound, and a tertiary amine compound; and
    separating the water phase and the hydrophobic solvent phase.

15. The method of claim 14, wherein diffusing water from the feed solution through the semi-permeable membrane and into the draw solution comprises controlling a concentration of the hydrophilic solvent of the draw solution to draw the water from the feed solution by forward osmosis.

16. The method of claim 14, further comprising delivering the water phase to a filtration device comprising a reverse osmosis membrane to remove a trace amount of one or more of the hydrophobic solvent and the hydrophilic solvent and form a purified water product.

17. The method of claim 14, further comprising introducing $CO_2$ and one or more of additional water and additional alcohol to the hydrophobic solvent phase after separating the water phase and the hydrophobic solvent phase to form an additional draw solution comprising additional hydrophilic solvent and the one or more of the additional water and the additional alcohol.

18. The method of claim 14, wherein diffusing water from the feed solution through the semi-permeable membrane and into the draw solution through forward osmosis further comprises diffusing at least one organic solute from the feed solution through the semi-permeable membrane and into the draw solution, wherein the hydrophobic solvent phase further comprises the at least one organic solute diffused from the feed solution.

19. The method of claim 18, further comprising:
introducing $CO_2$ and one or more of additional water and additional alcohol to the hydrophobic solvent phase to form a second multiple-phase solution comprising an organic concentrate and an additional draw solution comprising additional hydrophilic solvent and the one or more of the additional water and the additional alcohol; and
separating the additional draw solution and the organic concentrate.

20. The method of claim 1, wherein providing the single-phase draw solution comprising the one or more of the amidinium salt, the guanidinium salt, and the tertiary aminium salt to the second side of the membrane comprises forming the single-phase draw solution to comprise from about 0.5 molal to about 20.0 molal of the one or more of the amidinium salt, the guanidinium salt, and the tertiary aminium salt.

21. The method of claim 20, wherein forming the single-phase draw solution to comprise from about 0.5 molal to about 20.0 molal of the one or more of the amidinium salt, the guanidinium salt, and the tertiary aminium salt comprises forming the single-phase draw solution to have an osmotic pressure of greater than or equal to about 1.0 Osm/kg.

22. The method of claim 1, wherein providing the single-phase draw solution comprising the one or more of the amidinium salt, the guanidinium salt, and the tertiary aminium salt to the second side of the membrane comprises selecting a polyatomic cation of the one or more of the amidinium salt, the guanidinium salt, and the tertiary aminium salt to have a nitrogen atom to carbon atom ratio of from about 1:2 to about 1:15.

23. The method of claim 1, wherein providing the single-phase draw solution comprising the one or more of the amidinium salt, the guanidinium salt, and the tertiary aminium salt to the second side of the membrane comprises selecting the single-phase draw solution to comprise one or more of a tertiary aminium carbonate, a tertiary aminium bicarbonate, and a tertiary aminium alkyl carbonate.

24. The method of claim 23, wherein selecting the single-phase draw solution to comprise one or more of the tertiary aminium carbonate, the tertiary aminium bicarbonate, and the tertiary aminium alkyl carbonate comprises selecting a tertiary aminium cation of the one or more of the tertiary aminium carbonate, the tertiary aminium bicarbonate, and the tertiary aminium alkyl carbonate to have one nitrogen atom and less than or equal to eight carbon atoms.

25. The method of claim 1, wherein providing the single-phase draw solution comprising one or more of the amidinium salt, the guanidinium salt, and the tertiary aminium salt to the second side of the membrane comprises selecting the single-phase draw solution to comprise one or more of an amidinium carbonate, an amidinium bicarbonate, an amidinium alkyl carbonate, a guanidinium carbonate, a guanidinium bicarbonate, and a guanidinium alkyl carbonate.

* * * * *

UNITED STATES PATENT AND TRADEMARK OFFICE
CERTIFICATE OF CORRECTION

PATENT NO. : 10,363,336 B2
APPLICATION NO. : 13/480053
DATED : July 30, 2019
INVENTOR(S) : Aaron D. Wilson, Frederick F. Stewart and Mark L. Stone Page 1 of 1

It is certified that error appears in the above-identified patent and that said Letters Patent is hereby corrected as shown below:

In the Specification
Column 16, Line 30, change "solution was nm" to --solution was run--

Signed and Sealed this
Tenth Day of September, 2019

Andrei Iancu
*Director of the United States Patent and Trademark Office*